US006933148B2

(12) United States Patent
Collins et al.

(10) Patent No.: US 6,933,148 B2
(45) Date of Patent: Aug. 23, 2005

(54) CELL SEPARATION COMPOSITIONS AND METHODS

(75) Inventors: Daniel P. Collins, Lino Lakes, MN (US); Joel H. Hapke, Brooklyn Center, MN (US); Carol A. Buchert, Ramsey, MN (US)

(73) Assignee: BioErgonomics, Inc., St. Paul, MN (US)

( * ) Notice: Subject to any disclaimer, the term of this patent is extended or adjusted under 35 U.S.C. 154(b) by 0 days.

(21) Appl. No.: 10/672,317

(22) Filed: Sep. 26, 2003

(65) Prior Publication Data

US 2004/0062766 A1 Apr. 1, 2004

Related U.S. Application Data

(60) Provisional application No. 60/414,692, filed on Sep. 27, 2002.

(51) Int. Cl.$^7$ .............................. C12N 5/06; C12N 5/08
(52) U.S. Cl. ........................ 435/372; 424/93.71; 435/2; 435/7.23; 435/7.24; 435/7.25; 435/355; 435/372.1; 435/372.2; 435/372.3
(58) Field of Search ...................... 424/93.71; 435/7.23, 435/7.24, 7.25, 355, 372, 372.1, 372.2, 372.3, 2

(56) References Cited

U.S. PATENT DOCUMENTS

| | | | |
|---|---|---|---|
| 4,946,778 A | | 8/1990 | Ladner et al. |
| 5,840,502 A | | 11/1998 | Van Vlasselaer |
| 5,877,299 A | | 3/1999 | Thomas et al. |
| 6,117,985 A | * | 9/2000 | Thomas et al. ............. 530/413 |
| 6,146,628 A | | 11/2000 | Uckun et al. |
| 6,153,113 A | | 11/2000 | Goodrich et al. |
| 6,280,622 B1 | | 8/2001 | Goodrich et al. |
| 6,448,075 B1 | * | 9/2002 | Thomas et al. ............. 435/325 |
| 6,491,917 B1 | | 12/2002 | Thomas et al. |
| 2003/0027233 A1 | * | 2/2003 | Collins et al. ............. 435/7.92 |

FOREIGN PATENT DOCUMENTS

WO      WO 02/83262      * 10/2002

OTHER PUBLICATIONS

Bigbee et al., "Monoclonal Antibodies Specific for the M– and N–Forms of Human Glycophorin A," Mol. Immunol., 1983, 20:1353–1362.

Cole et al., "The EBV–Hybridoma Technique and Its Application to Human Lung Cancer," Monoclonal Antibodies and Cancer Therapy, 1985, pp. 77–96.

Cote et al., "Generation of human monoclonal antibodies reactive with cellular antigens," Proc. Natl. Acad. Sci. USA, 1983, 80:2026–2030.

Collins, "Cytokine and cytokine receptor expression as a biological indicator of immune activation: important considerations in the development of in vitro model systems," J. Immunol. Meth., 2000, 243:125–145.

Eggens et al., "Specific Interaction between Le$^x$ and Le$^x$ Determinants, A Possible Basis for Cell Recognition in Preimplantation Embryos and In Embryonal Carcinoma Cells," J. Biol. Chem., 1989, 264:9476–9484.

Huse et al., "Generation of a Large Combinatorial Library of the Immunoglobulin Repertoire in Phage Lambda," Science, 1989, 246:1275–1281.

Jennings et al., "CD9 cluster workshop report: cell surface binding and functional analysis," Leukocyte Typing V, 1995, Oxford University Press, Oxford, pp. 1249–1251.

Kannagi et al., "A Series of Human Erythrocyte Glycosphingolipids Reacting to the Monoclonal Antibody Directed to a Developmentally Regulated Antigen, SSEA–1," J. Biol. Chem., 1982, 257:14865–14874.

Kishimoto (chairman), 6$^{th}$ International Workshop and Conference on Human Leukocyte Differentiation Antigens, Nov. 10–14, 1996, Kobe, Japan (TOC only).

Knapp et al. (eds.), Leukocyte Typing IV, 1989, Oxford University Press, Oxford (TOC only).

Köhler and Milstein, "Continuous cultures of fused cells secreting antibody of predefined specificity," Nature, 1975, 256:495–497.

Kozbor and Roder, "The production of monoclonal antibodies from human lymphocytes," Immunology Today, 1983, 4:72–79.

Lanza et al., "cDNA Cloning and Expression of Platelet p24/CD9, Evidence for a New Family of Multiple Membrane–Spanning Proteins," J. Biol. Chem., 1991, 266:10638–10645.

Magnani et al., "Monoclonal Antibodies PMN 6, PMN 29, and PM–81 Bind Differently to Glycolipids Containing a Sugar Sequence Occurring in Lacto–N–Fucopentaose III," Arch. Biochem. Biophys., 1984, 233:501–506.

Outram et al., "Erythromyeloid Lineage Fidelity is Conserved in Erythroleukaemia," Leukocyte Research, 1988, 12:651–657.

Reinherz et al. (eds.), Leukocyte Typing II, 1986, Springer–Verlag, New York (TOC only).

Rubinstein et al., "Anti–Platelet Antibody Interactions with Fcγ Receptor," Seminars in Thrombosis and Hemostasis, 1995, 21:10–12.

Solter and Knowles, "Monoclonal antibody defining a stage–specific mouse embryonic antigen (SSEA–1)," Proc. Natl. Acad. Sci. USA, 1978, 75:5565–5569.

Telen and Bolk, "Human red cell antigens," Transfusion, 1987, 27:309–314.

Vettese–Dadey, "Going Their Separate Ways: A Profile of Products for Cell Separation," The Scientist, 1999, vol. 13, No. 18, 10 pages.

Von dem Borne and Modderman, "Cluster Report: CD9," Leukocyte Typing IV, 1989, ed. Knapp et al, Oxford University Press, Oxford, pp. 989–992.

Wagner, "Umbilical Cord Blood Stem Cell Transplantation," Am. J. Ped. Hematol. Oncol., 1993, 15:169–174.

Wright and Tomlinson, "The ins and outs of the transmembrane 4 superfamily," Immunology Today, 1994, 15:588–594.

* cited by examiner

Primary Examiner—David Saunders
(74) Attorney, Agent, or Firm—Fish & Richardson, P.C., P.A.

(57) ABSTRACT

The invention provides compositions and methods for cell separation. These reagents and techniques specifically agglutinate cells via surface antigen recognition and can be used to recover even rare cell types in high yield.

50 Claims, 4 Drawing Sheets

CELL SEPARATION COMPOSITIONS AND METHODS

This is a utility application, which claims priority to U.S. Provisional Patent Application Ser. No. 60/414,692, filed Sep. 27, 2002, of which is incorporated herein by reference in its entirety.

TECHNICAL FIELD

The present invention relates to compositions and methods for separating cells.

BACKGROUND

Many conventional blood cell isolation procedures include a preliminary bulk separation of erythrocytic and granulocytic components by density-gradient sedimentation. Density-gradient separation relies on small differences in the density of different cell types causing them to segregate at different levels in a fluid medium of variable density. Differences in density between the cell types can be small, and individual cells types can be heterogeneous in size and density. Consequently, particular cell types can become distributed throughout a density-gradient medium rather than precisely segregating at a discrete area in the density medium. This phenomenon can result in poor recovery of desired cells and/or contamination with undesired cell types. In procedures that enrich for rare blood cell types such as hematopoietic progenitor cells, density-gradient sedimentation generally results in poor yields. For example, using conventional density-gradient methods to isolate progenitor cells (e.g., CD34+ hematopoietic stem cells) from umbilical cord blood reportedly results in a significant loss of the desired stem cells. See e.g., Wagner, J. E., *Am J Ped Hematol Oncol* 15:169 (1993). As another example, using conventional density-gradient methods to isolate lymphocytes reportedly results in selective loss of particular lymphocyte subsets. See e.g., Collins, D. P., *J Immunol Methods* 243:125 (2000).

Increasing the recovery of rare cell types from donor tissue could dramatically improve the success of transplant and immune therapies (e.g., bone marrow transplants, stem cell-based gene therapy, and immune cell therapy), the success of which apparently is related to the actual number of the cells being used for therapy

SUMMARY

The invention provides compositions and methods for separating cells. The disclosed compositions and methods can be used, for example, to efficiently prepare cells for tissue culture, immunophenotypic characterization, other diagnostic testing, further purification, and therapeutic administration.

Methods of the invention include contacting a blood cell-containing sample (e.g., peripheral blood sample, umbilical cord sample, and bone marrow sample) with a cell separation composition. Without being bound by a particular mechanism, compositions of the invention can selectively agglutinate cells via interaction with cell surface antigens and/or by stimulating cell-cell adherence (e.g., via increased expression of cell surface adhesion factors). Agglutinated cells partition away from unagglutinated cells, which remain in solution. Cells can be recovered from either or both the agglutinate or the supernatant phase.

The disclosed compositions and methods can be used to isolate and enrich for a variety of cell types, including, for example, T lymphocytes, T helper cells, T suppressor cells, B cells, hematopoietic stem cells, circulating fetal cells in maternal circulation, and circulating metastatic tumor cells. The disclosed compositions and methods can be used in the context of allogenic and autologous transplantation. In the context of autologous transplantation, the disclosed compositions and methods can be used, for example, to remove undesired cells such as metastatic cancer cells from a patient's blood or bone marrow. Desirable cells (e.g., hematopoietic stem cells) then can be returned back to a patient without, or substantially free of, life-threatening tumor cells. The disclosed compositions and methods can be applied to cells of any mammal, including humans, non-human primates, rodents, swine, bovines and equines.

Cell separation compositions can contain dextran, anti-glycophorin A antibody, as well as one or more antibodies against cell surface antigens such as CD9, CD15, CD2, CD3, CD4, CD8, CD72, CD16, CD41a, HLA Class I, HLA-DR, CD29, CD11a, CD11b, CD11c, CD19, CD20, CD23, CD39, CD40, CD43, CD44, CDw49d, CD53, CD54, CD62L, CD63, CD66, CD67, CD81, CD82, CD94, CD99, CD100, CD161, Leu-13, TPA-1, or surface Ig, and combinations thereof.

For example, a composition can include dextran, anti-glycophorin A antibody, anti-CD15 antibody, anti-CD9 antibody, anti-CD94 antibody, and anti-CD161 antibody. In some embodiments, such a composition further can include an anti-CD72 antibody or anti-CD2 antibody. In other embodiments, such a composition further can include anti-CD4 antibody, anti-CD16 antibody, and anti-CD19 antibody, or anti-CD8 antibody, anti-CD16 antibody, and anti-CD19 antibody Cell separation compositions can contain antibodies against surface antigens of other types of cells (e.g., cell surface proteins of tumor cells).

Antibodies against cell surface antigens can be included in a cell separation composition in either or both soluble and substrate-bound forms. Antibodies can be bound to substrates such as latex microparticles, acid-etched glass particles, aggregated polypeptides, polysaccharides, avidin particles, or biotinylated agarose gel particles. Antibodies in cell separation compositions can be monoclonal and can be IgM or IgG antibodies. In some embodiments, a cell separation composition contains anti-human antibody. The concentration of a soluble antibody in a cell separation composition can be about 0.01 mg/L to about 15 mg/L. Substrate-bound antibodies can be included in a cell separation composition at a concentration between about 0.1 and about $50.0 \times 10^9$ particles/l.

Cell separation compositions also can contain heparin, divalent cations (e.g., $Ca^{+2}$, $Mg^{+2}$), and phosphate buffered saline. In some embodiments, compositions have a pH between 6.8 to 7.8 (e.g., between 7.2 to 7.4).

The invention also provides kits containing components of a cell separation composition and packaging material.

Kits can include a blood collection vessel such as a blood bag or a vacuum tube.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention features compositions and methods for separating cells. Compositions of the invention can be used to selectively agglutinate cells from blood cell-containing samples. Without being bound by a particular mechanism, compositions of the invention can agglutinate cells via interaction with cell surface antigens and/or by stimulating expression of cell surface adhesion factors such as LFA-1 (Lymphocyte Function-Associated Antigen-1, CD11a/CD18) and ICAM-1 (Intercellular Adhesion Molecule-1, CD54). Agglutinated cells partition away from unagglutinated cells, which remain in solution. Cells can be recovered from the supernatant or from the agglutinate.

Cell Separation Compositions

A cell separation composition in accord with the invention can contain dextran and one or more antibodies against (i.e., that have specific binding affinity for) a cell surface antigen.

Dextran is a polysaccharide consisting of glucose units linked predominantly in alpha (1 to 6) mode. Dextran can cause stacking of erythrocytes (i.e., rouleau formation) and thereby facilitate the removal of erythroid cells from solution. Typically, the concentration of dextran in a cell separation composition is 10 to 20 g/L (e.g., 20 g/L). Antibodies against cell surface antigens can facilitate the removal of blood cells from solution via homotypic agglutination (i.e., agglutination of cells of the same cell type) and/or heterotypic agglutination (i.e., agglutination of cells of different cell types).

Cell separation compositions can contain antibodies against blood cell surface antigens including, for example, glycophorin A, CD15, CD9, CD2, CD3, CD4, CD8, CD72, CD16, CD41a, HLA Class I, HLA-DR, CD29, CD11a, CD11b, CD11c, CD19, CD20, CD23, CD39, CD40, CD43, CD44, CDw49d, CD53, CD54, CD62L, CD63, CD66, CD67, CD81, CD82, CD94, CD99, CD100, CD161, Leu-13, TPA-1, surface Ig, and combinations thereof. Thus, cell separation compositions can be formulated to selectively agglutinate particular types of blood cells.

In some embodiments, a cell separation composition includes antibodies against glycophorin A. Typically, the concentration of anti-glycophorin A antibodies in a cell separation composition ranges from 0.1 to 15 mg/L (e.g., 0.1 to 10 mg/L, 1 to 5 mg/L, or 1 mg/L). Anti-glycophorin A antibodies can facilitate the removal of red cells from solution by at least two mechanisms. Anti-glycophorin A antibodies can cause homotypic agglutination of erythrocytes since glycophorin A is the major surface glycoprotein on erythrocytes. In addition, anti-glycophorin A antibodies also can stabilize dextran-mediated rouleau formation. Exemplary monoclonal anti-glycophorin A antibodies include, without limitation, 107FMN (Murine IgG1 Isotype), YTH89.1 (Rat IgG2b Isotype), and E4 (Murine IgM Isotype). See e.g., M. Vanderlaan et al., *Molecular Immunology* 20:1353 (1983); Telen M. J. and Bolk, T. A., *Transfusion* 27: 309 (1987); and Outram S. et al., *Leukocyte Research* 12:651 (1988).

In some embodiments, a cell separation composition includes antibodies against CD15. The concentration of anti-CD15 antibodies in a cell separation composition can range from 0.1 to 15 mg/L (e.g., 0.1 to 10, 1 to 5, or 1 mg/L). Anti-CD15 antibodies can cause homotypic agglutination of granulocytes by crosslinking CD15 molecules that are present on the surface of granulocytes. Anti CD15 antibodies also can cause homotypic and heterotypic agglutination of granulocytes with monocytes, NK-cells and B-cells by stimulating expression of adhesion molecules (e.g., L-selectin and beta-2 integrin) on the surface of granulocytes that interact with adhesion molecules on monocytes, NK-cells and B-cells. Heterotypic agglutination of these cell types can facilitate the removal of these cells from solution along with red cell components. Exemplary monoclonal anti-CD15 antibodies include, without limitation, AHN1.1 (Murine IgM Isotype), FMC-10 (Murine IgM Isotype), BU-28 (Murine IgM Isotype), MEM-157 (Murine IgM Isotype), MEM-158 (Murine IgM Isotype), MEM-167 (Murine IgM Isotype). See e.g., *Leukocyte typing IV* (1989); *Leukocyte typing II* (1984); *Leukocyte typing VI* (1995); Solter D. et al., *Proc. Natl. Acad. Sci.* USA 75:5565 (1978); Kannagi, R. et al., *J. Biol. Chem.* 257:14865 (1982); Magnani, J. L. et al., Archives of Biochemistry and Biophysics 233:501 (1984); Eggens, I. et al., *J. Biol. Chem.* 264:9476 (1989).

In some embodiments, a cell separation composition includes antibodies against CD9 (e.g., at a concentration ranging from 0.1 to 15, 0.1 to 10, 1 to 5, or 1 mg/L). Anti-CD9 antibodies can cause homotypic agglutination of platelets. Anti-CD9 antibodies also can cause heterotypic agglutination of granulocytes and monocytes via platelets that have adhered to the surface of granulocytes and monocytes. CD9 antibodies can promote the expression of platelet l-selectin, which facilitates the binding of platelets to leukocyte cell surfaces. Thus, anti-CD9 antibodies can promote multiple cell-cell linkages and thereby facilitate agglutination and removal from solution. Exemplary monoclonal anti-CD9 antibodies include, without limitation, MEM-61 (Murine IgG1 Isotype), MEM-62 (Murine IgG1 Isotype), MEM-192 (Murine IgM Isotype), FMC-8 (Murine IgG2a Isotype), SN4 (Murine IgG1 Isotype), BU-16 (Murine IgG2a Isotype). See e.g., *Leukocyte typing VI* (1995); *Leukocyte typing II* (1984); Von dem Bourne A. E. G. Kr. and Moderman P. N. (1989) In *Leukocyte typing IV* (ed. W. Knapp, et al), pp. 989–92. Oxford University Press, Oxford; Jennings, L. K., et al. In *Leukocyte typing V*, ed. S. F. Schlossmann et al., pp. 1249–51. Oxford University Press, Oxford (1995); Lanza, F. et al., *J. Biol. Chem.* 266:10638 (1991); Wright et al., *Immunology Today* 15:588 (1994); Rubinstein, E. et al., *Seminars in Thrombosis and Hemostasis* 21:10 (1995).

In some embodiments, a cell separation composition contains antibodies against CD41, which can selectively agglutinate platelets. In some embodiments, a cell separation composition contains antibodies against CD3, which can selectively agglutinate T-cells. In some embodiments, a cell separation composition contains antibodies against CD2, which can selectively agglutinate T-cells and NK cells. In some embodiments, a cell separation composition contains antibodies against CD72, which can selectively agglutinate B-cells. In some embodiments, a cell separation composition contains antibodies against CD16, which can selectively agglutinate NK cells and neutrophilic granulocytes. The concentration of each of these antibodies can range from 0.01 to 15 mg/L.

In other embodiments, a cell separation composition includes antibodies against CD94 and CD161, which can selectively agglutinate subsets of NK cells. Clone HP-3D9 is an example of a suitable anti-CD94 antibody. Clone B199.2 is an example of a suitable anti-CD161 antibody. Monoclonal anti-CD94 and anti-CD161 antibodies are particularly useful. Typically, the concentration of each of these antibodies ranges from 0.01 mg/L to 10 mg/L (e.g., 0.1 to 5, 0.1 to 2.5, 0.1 to 1.5 mg/L). For example, the concentration of anti-CD94 antibody can be 0.125 to 0.25 mg/L. The concentration of an anti-CD161 antibody can be 0.25 to 1 mg/L.

As mentioned above, cell separation compositions can be formulated to selectively agglutinate particular blood cells. As an example, a cell separation composition containing dextran and antibodies against glycophorin A, CD15, and CD9 can facilitate the agglutination of erythrocytes, granulocytes, NK cells, B cells, and platelets. T cells, NK cells and rare precursor cells then can be recovered from solution. If the formulation also contained an antibody against CD3, T cells also could be agglutinated, and NK cells and rare precursors could be recovered from solution. In other embodiments, a cell separation composition includes dextran and antibodies against glycophorin A, CD15, CD9, CD94, and CD161 such that erythrocytes, granulocytes, NK cells, B cells, and platelets are agglutinated and T cells and rare precursor cells can be recovered from the solution. To obtain purified populations of CD4 T cells, anti-CD8 antibodies, anti-CD16 antibodies, and anti-CD19 antibodies can be included in the composition. To obtain purified populations of CD8 T cells, anti-CD4 antibodies, anti-CD16 antibodies, and anti-CD19 antibodies can be included in the composition. Non-limiting examples of suitable anti-CD4 antibodies include clones QS4120, RPA-T4, S3.5, M-T441, RFT-4, and 13B8.2. Non-limiting examples of suitable anti-CD8 antibodies include clones HIT8a, UCHT4, and RPA-T8. Clone 3G8 is an example of a suitable anti-CD16 antibody. Non-limiting examples of suitable anti-CD19 antibodies includes clones HIB19 and BU12.

Cell separation compositions can contain antibodies against surface antigens of other types of cells (e.g., cell surface proteins of tumor cells). Those of skill in the art can use routine methods to prepare antibodies against cell surface antigens of blood, and other, cells from humans and other mammals, including, for example, non-human primates, rodents (e.g., mice, rats, hamsters, rabbits and guinea pigs), swine, bovines, and equines.

Typically, antibodies used in the composition are monoclonal antibodies, which are homogeneous populations of antibodies to a particular epitope contained within an antigen. Suitable monoclonal antibodies are commercially available, or can be prepared using standard hybridoma technology. In particular, monoclonal antibodies can be obtained by techniques that provide for the production of antibody molecules by continuous cell lines in culture, including the technique described by Kohler, G. et al., *Nature*, 1975, 256:495, the human B-cell hybridoma technique (Kosbor et al., *Immunology Today* 4:72 (1983); Cole et al., *Proc. Natl. Acad. Sci. USA* 80:2026 (1983)), and the EBV-hybridoma technique (Cole et al., "Monoclonal Antibodies and Cancer Therapy," Alan R. Liss, Inc., pp. 77–96 (1983)).

Antibodies can be of any immunoglobulin class including IgG, IgM, IgE, IgA, IgD, and any subclass thereof. Antibodies of the IgG and IgM isotypes are particularly useful in cell separation compositions of the invention. Pentameric IgM antibodies contain more antigen binding sites than IgG antibodies and can, in some cases (e.g., anti-glycophorin A and anti-CD15), be particularly useful for cell separation reagents. In other cases (e.g., anti-CD9 antibodies), antibodies of the IgG isotype are particularly useful for stimulating homotypic and/or heterotypic agglutination.

Antibodies against cell surface antigens can be provided in liquid phase (i.e., soluble) or can be provided in association with a solid phase (i.e., substrate-bound). Liquid phase antibodies typically are provided in a cell separation composition at a concentration between about 0.01 and about 15 mg/L (e.g., between 0.25 to 10, 0.25 to 1, 0.5 to 2, 1 to 2, 4 to 8, 5 to 10 mg/L). Substrate-bound antibodies typically are provided in a cell separation composition at a concentration between about 0.1 and about $50.0 \times 10^9$ particles/L (e.g., between 0.25 to $10.0 \times 10^9$, 1 to $20.0 \times 10^9$, 2 to $10.0 \times 10^9$, 0.5 to $2 \times 10^9$, 2 to $5 \times 10^9$, 5 to $10 \times 10^9$, and 10 to $30 \times 10^9$ particles/L), where particles refers to solid phase particles having antibodies bound thereto.

Antibodies against different cell surface antigens can be covalently linked to a solid phase to promote crosslinking of cell surface molecules and activation of cell surface adhesion molecules. The use of substrate-bound antibodies can facilitate cell separation (e.g., by virtue of the mass that the particles contribute to agglutinated cells, or by virtue of properties useful for purification).

In some embodiments, the solid phase with which an substrate-bound antibody is associated is particulate. In some embodiments, an antibody is bound to a latex microparticle such as a paramagnetic bead (e.g., via biotin-avidin linkage, covalent linkage to COO groups on polystyrene beads, or covalent linkage to $NH_2$ groups on modified beads). In some embodiments, an antibody is bound to an acid-etched glass particle (e.g., via biotin-avidin linkage). In some embodiments, an antibody is bound to an aggregated polypeptide such as aggregated bovine serum albumin (e.g., via biotin-avidin linkage, or covalent linkage to polypeptide COO groups or $NH_2$ groups). In some embodiments, an antibody is covalently linked to a polysaccharide such as high molecular weight (e.g., >1,000,000 $M_r$) dextran sulfate. In some embodiments, biotinylated antibodies are linked to avidin particles, creating tetrameric complexes having four antibody molecules per avidin molecule. In some embodiments, antibodies are bound to biotinylated agarose gel particles (One Cell Systems, Cambridge, Mass., U.S.A.) via biotin-avidin-biotinylated antibody linkages. Such particles typically are about 300–500 microns in size, and can be created in a sonicating water bath or in a rapidly mixed water bath.

Cell-substrate particles (i.e., particles including cells and substrate-bound antibodies) can sediment from solution as an agglutinate. Cell-substrate particles also can be removed from solution by, for example, an applied magnetic field, as when the particle is a paramagnetic bead.

Cell separation compositions also can contain divalent cations (e.g., $Ca^{+2}$ and $Mg^{+2}$). Divalent cations can be provided, for example, by a balanced salt solution (e.g., Hank's balanced salt solution). $Ca^{+2}$ ions may be important for selectin-mediated and integrin-mediated cell-cell adherence.

Cell separation compositions of the invention also can contain an anticoagulant such as heparin. Heparin can prevent clotting and non-specific cell loss associated with clotting in a high calcium environment. Heparin also promotes platelet clumping. Clumped platelets can adhere to granulocytes and monocytes and thereby enhance heterotypic agglutination more so than single platelets. Heparin can be supplied as a heparin salt (e.g., sodium heparin, lithium heparin, or potassium heparin).

Cell Separation Methods

The disclosed compositions can be used, for example, to efficiently prepare cells for tissue culture, immunophenotypic characterization, diagnostic testing, further purification, and therapeutic administration. Without being bound by a particular mechanism, compositions of the invention can selectively agglutinate cells via interaction with cell surface antigens and/or by stimulating cell-cell adherence (e.g., via increased expression of cell surface adhesion factors). Agglutinated cells partition away from unagglutinated cells, which remain in solution.

After agglutination, unagglutinated cells can be recovered from the solution phase (i.e., the supernatant). In embodiments in which one or more biotinylated antibodies are used, the supernatant can be contacted with a composition containing avidin or streptavidin coated particles (e.g., magnetic beads) to further deplete the supernatant of undesired cells. After mixing the supernatant and composition, the beads can be separated from the supernatant (e.g., by applying a magnet) and cells can be removed from the supernatant.

Cells also can be recovered from the agglutinate. Agglutinated cells can be dissociated by, for example, transferring the cells into buffers that contain divalent cation chelators such as EDTA or EGTA. Cells recovered from the agglutinate can be further separated by using antibodies against cell surface antigens. Cells can be recovered from a gel microparticle-antibody-cell agglutinate by heating the agglutinate to a temperature just above the melting point.

The disclosed compositions can be used to separate cells from a variety of blood-cell containing samples, including peripheral blood (e.g., obtained by venipuncture), umbilical cord blood (e.g., obtained post-gravida), and bone marrow (e.g., from aspirate). Blood cell-containing samples can be contacted with a cell separation composition to cause agglutination of particular types of cells. For example, erythrocytes and differentiated myeloid blood constituents can be selectively agglutinated using cell separation compositions containing antibodies to surface antigens of these cells. The disclosed compositions and methods can be used to isolate and enrich for a variety of cell types, including, for example, T lymphocytes, T helper cells, T suppressor cells, B cells, hematopoietic stem cells, circulating fetal cells in maternal circulation, and circulating metastatic tumor cells. The disclosed compositions can be used to agglutinate cells of any mammal, including humans, non-human primates, rodents, swine, bovines, and equines.

The disclosed compositions and methods can be used in the context of allogenic and autologous transplantation. In the context of autologous transplantation, the disclosed compositions and methods can be used, for example, to remove undesired cells such as metastatic cancer cells from a patient's blood or bone marrow. Desirable cells (e.g., hematopoietic stem cells) then can be returned back to a patient without, or substantially free of, life-threatening tumor cells.

Cell separation compositions containing antibodies against cell surface proteins of tumor cells can be used to purge tumor cells from a patient's blood or bone marrow. Such compositions also can be used for diagnostic procedures to, for example, obtain and detect tumor cells in an agglutinate, where they are concentrated and are therefore more easily detectable than in circulating blood or in bone marrow. A cell separation composition containing antibodies against the receptor for epithelial growth factor can be used to agglutinate tumor cells derived from epithelial tumors (e.g., head and neck tumors). A cell separation composition containing antibodies against estrogen receptors can be used to agglutinate tumor cells derived from breast and ovarian tumors. A cell separation composition containing antibodies against surface immunoglobulins can be used to agglutinate tumor cells associated with chronic lymphocytic leukemia, plasmacytoma, and multiple myeloma. Breast carcinoma cells express CD15 on their cell surface, and can be purged from bone marrow using cell separation compositions that contain antibodies against CD15. Other formulas can be made on the basis of cell type and cell surface proteins to obtain or deplete metastatic tumor cells derived from other carcinomas (e.g., erythroleukemia, endothelial carcinoma, or gastrointestinal carcinoma) from a patient's blood or bone marrow.

Cell Separation Kits

A cell separation composition can be combined with packaging material and sold as a kit. The components of a cell separation composition can be packaged individually or in combination with one another. In some embodiments, the packaging material includes a blood collection vessel (e.g., blood bag, vacuum tube). The packaging material included in a kit typically contains instructions or a label describing how the cell separation composition can be used to agglutinate particular types of cells. Components and methods for producing such kits are well known.

The invention is further described in the following examples, which do not limit the scope of the invention described in the claims.

EXAMPLES

Example 1

Separating Blood Cells

This example describes the general method by which cells were separated using the cell separation reagents described below. An equal volume of a cell separation reagent (i.e., 25 ml) was combined with an equal volume of an ethylenediaminetetraacetic acid (EDTA) anti-coagulated heparinized peripheral blood sample (i.e., 25 ml) in a 50 ml conical tube. Samples containing white blood cell counts greater than $20 \times 10^6$ cells/ml were combined one part blood with two parts cell separation reagent. Tubes were gently mixed on a rocker platform for 20 to 45 minutes at room temperature. Tubes were stood upright in a rack for 30 to 50 minutes to permit agglutinated cells to partition away from unagglutinated cells, which remained in solution. Without disturbing the agglutinate, a pipette was used to recover unagglutinated cells from the supernatant. Recovered cells were washed in 25 ml PBS and centrifuged at 500×g for 7 minutes. The cell pellet was resuspended in 4 ml PBS.

In embodiments in which one or more of the antibodies are biotinylated, avidin coated magnetic beads were added to the supernatant (1 mL beads/mL of starting sample). Beads and supernatant were mixed on a platform rocker for 20 minutes. Beads and beads bound to undesired cells were removed by placing the tube containing the mixture in a PrepaMag™ for 5 minutes. Beads and beads bound to undesired cells were drawn to the sides of the tube. A pipet was used to draw the fluid from the center and bottom of each tube, with care taken not to disturb the beads and cells on the sides of the tube.

Cells also were recovered from the agglutinate using a hypotonic lysing solution containing EDTA and ethylene glycol-bis(2-aminoethylether)-N,N,N',N'-tetraacetic acid (EGTA). Agglutinated cells were treated with 25 ml VitaLyse™ (BioErgonomics, St. Paul, Minn.) and vortexed. After 10 minutes, cells either were exposed to an applied magnetic field to recover cells associated with antibodies bound to paramagnetic beads, or were centrifuged at 500×g for 7 minutes and the supernatant was removed. In either case, cells were resuspended in 4 ml PBS.

Recoveries of erythrocytes, leukocytes, lymphocytes, monocytes, granulocytes, T cells, B cells, and NK cells were determined by flow cytometry and immunophenotyping.

Prior to flow cytometry, leukocyte recovery (i.e., white blood cell count) was determined using a Coulter Onyx Hematology Analyzer, and samples were adjusted with PBS to a cell count of $1 \times 10^7$ cells/mL. 100 $\mu$l aliquots of volume-adjusted sample were stained at room temperature in the dark for 15 to 30 minutes with either FITC labeled anti-CD3 antibodies (reactive to T cells), PE labeled anti-CD19 antibodies (reactive to B cells), or PE labeled anti-CD16 antibodies (reactive to NK cells). 2 ml of PBS was added to each sample, and the sample then was vortexed and centrifuged to pellet cells. Supernatants were discarded, and cell pellets were vortexed and resuspended in 0.5 ml PBS. Stained and unstained cells were analyzed by flow cytometry using a Coulter XL flow cytometer. Erythrocytes, leukocytes, lymphocytes, monocytes, granulocytes and platelets were identified on the basis of diagnostic forward and side light scatter properties. B cells, T cells, and NK cells were identified on the basis of light scattering and staining by labeled antibodies.

Example 2

Erythrocyte Agglutination

The reagent described in Table 1 was used to separate cells according to the method described in Example 1.

TABLE 1

| | |
|---|---|
| Dextran (average molecular weight 413,000) | 20 g/L |
| Dulbecco's phosphate buffered saline (10X) | 100 mL/L |
| Sodium Heparin (10,000 units/Ml) | 1 mL/L |
| Hank's balanced salt solution (pH 7.2–7.4) | 50 mL/L |
| Anti-human glycophorin A (murine IgM monoclonal antibody clone E4) | 1.0 mg/L |

Results of a separation are shown in Table 2. Erythrocytes were depleted 99.7% from the supernatant. Lymphocytes (T cells, B cells, and NK cells) were enriched in the supernatant relative to the monocytes and granulocytes.

TABLE 2

| | Before separation | After separation |
|---|---|---|
| Erythrocytes per mL | $4.41 \times 10^9$ | $0.015 \times 10^9$ |
| Leukocytes per mL | $5.9 \times 10^6$ | $5.3 \times 10^6$ |
| Lymphocytes (%) | 28.7 | 41.9 |
| Monocytes (%) | 8.69 | 4.78 |
| Granulocytes (%) | 62.5 | 52.6 |
| T Cells (CD3+) | 19.7 | 31.8 |
| B Cells (CD19+) | 4.46 | 5.42 |
| NK Cells (CD16+) | 3.15 | 5.9 |

Example 3

Erythrocyte and CD2+ Cell Agglutination

The reagent described in Table 3 was used to separate cells according to the method described in Example 1.

TABLE 3

| | |
|---|---|
| Dextran (average molecular weight 413,000) | 20 g/L |
| Dulbecco's phosphate buffered saline (10X) | 100 mL/L |
| Sodium Heparin (10,000 units/mL) | 1 mL/L |
| Hank's balanced salt solution (pH 7.2–7.4) | 50 mL/L |
| Anti-human glycophorin A (murine IgM monoclonal | 1.0 mg/L |

TABLE 3-continued antibody, clone E4
Anti-human CD2 paramagnetic agglutination particles (avidin-coated 4.3 micron diameter paramagnetic polystyrene particles labeled with saturating doses of biotin-labeled mouse anti-human CD2, clone d118.10.1)   14.02 × $10^9$ particles/L Results of a separation are shown in Table 4. In the supernatant, erythrocytes were depleted 99.7%, T cells were depleted 95.1%, and NK cells were depleted 69.1%. B cells were enriched in the supernatant relative to other cells.

TABLE 4

|  | Before separation | After separation |
| --- | --- | --- |
| Erythrocytes per mL | 4.41 × $10^9$ | 0.014 × $10^9$ |
| Leukocytes per mL | 5.9 × $10^6$ | 2.63 × $10^6$ |
| Lymphocytes (%) | 28.7 | 16.0 |
| Monocytes (%) | 8.69 | 6.04 |
| Granulocytes (%) | 62.5 | 75.6 |
| T Cells (CD3+) | 19.7 | 3.3 |
| B Cells (CD19+) | 4.46 | 9.63 |
| NK Cells (CD16+) | 3.15 | 4.32 |

Example 4

Erythrocyte and CD72+ Cell Agglutination

The reagent described in Table 5 was used to separate cells according to the method described in Example 1.

TABLE 5

| | |
| --- | --- |
| Dextran (average molecular weight 413,000) | 20 g/L |
| Dulbecco's phosphate buffered saline (10X) | 100 mL/L |
| Sodium Heparin (10,000 units/mL) | 1 mL/L |
| Hank's balanced salt solution (pH 7.2–7.4) | 50 mL/L |
| Anti-human glycophorin A (murine IgM monoclonal antibody, clone E4) | 1.0 mg/L |
| Anti-human CD72 paramagnetic agglutination particles (avidin-coated 4.3 micron diameter paramagnetic polystyrene particles labeled with saturating doses of biotin-labeled mouse anti-human CD72, clone BU40) | 2.63 × $10^6$ particles/mL |

Results of a separation are shown in Table 6. In the supernatant, erythrocytes were depleted 99.5%, and B cells were depleted 81.6%.

TABLE 6

|  | Before separation | After separation |
| --- | --- | --- |
| Erythrocytes per mL | 4.41 × $10^9$ | 0.021 × $10^9$ |
| Leukocytes per mL | 5.9 × $10^6$ | 3.2 × $10^6$ |
| Lymphocytes (%) | 28.7 | 47.0 |
| Monocytes (%) | 8.69 | 4.78 |
| Granulocytes (%) | 62.5 | 47.7 |
| T Cells (CD3+) | 19.7 | 41.3 |
| B Cells (CD19+) | 4.46 | 2.75 |
| NK Cells (CD16+) | 3.15 | 4.77 |

Example 5

Erythrocyte, CD15+ Cell, and CD9+ Cell Agglutination

The reagent described in Table 7 was used to separate cells according to the method described in Example 1.

TABLE 7

| | |
| --- | --- |
| Dextran (average molecular weight 413,000) | 20 g/L |
| Dulbecco's phosphate buffered saline (10X) | 100 mL/L |
| Sodium Heparin (10,000 units/ml) | 1 mL/L |
| Hank's balanced salt solution (pH 7.2–7.4) | 50 mL/L |
| Anti-human glycophorin A (murine IgM monoclonal antibody, clone E4) | 0.1–15 mg/L (preferably about 1.0 mg/L) |
| Anti-CD15 (murine IgM monoclonal antibody, clone MEM-158) | 0.1–15 mg/L (preferably about 1.0 mg/L) |
| Anti-CD9 (murine IgG monoclonal antibody, clone MEM-61) | 0.1–15 mg/L (preferably about 1.0 mg/L) |

Results of a separation are shown in Table 8. In the supernatant, erythrocytes were depleted 99.9%, monocytes and granulocytes were depleted 99.8%, B cells were depleted 74%, and NK cells were depleted 64.9%. In addition, platelets, present in the supernatant at 226×$10^6$/ml before separation, were depleted to 1.4×$10^6$/ml for 99.4% depletion.

TABLE 8

|  | Before separation | After separation |
| --- | --- | --- |
| Erythrocytes per mL | 4.41 × $10^9$ | 0.006 × $10^9$ |
| Leukocytes per mL | 5.9 × $10^6$ | 1.53 × $10^6$ |
| Lymphocytes (%) | 28.7 | 99.0 |
| Monocytes (%) | 8.69 | 0.12 |
| Granulocytes (%) | 62.5 | .083 |
| T Cells (CD3+) | 19.7 | 83.2 |
| B Cells (CD19+) | 4.46 | 8.10 |
| NK Cells (CD16+) | 3.15 | 8.43 |

Example 6

Erythrocyte, CD15+ Cell, CD9+ Cell, and CD2+ Cell Agglutination

The reagent described in Table 9 was used to separate cells according to the method described in Example 1.

TABLE 9

| | |
| --- | --- |
| Dextran (average molecular weight 413,000) | 20 g/L |
| Dulbecco's phosphate buffered saline (10X) | 100 mL/L |
| Sodium Heparin (10,000 units/mL) | 1 mL/L |
| Hank's balanced salt solution (pH 7.2–7.4) | 50 mL/L |
| Anti-human glycophorin A (murine IgM monoclonal antibody, clone E4) | 1 mg/L |
| Anti-CD15 (murine IgM monoclonal antibody, clone MEM-158) | 1 mg/L |
| Anti-CD9 (murine IgG monoclonal antibody, clone MEM-61) | 1 mg/L |
| Anti-human CD2 paramagnetic agglutination particles (avidin-coated 4.3 micron diameter paramagnetic polystyrene particles labeled with saturating doses of biotin-labeled mouse anti-human CD2, clone d118.10.1) | 14.02 × $10^9$ particles/L |

Results of a separation are shown in Table 10. In the supernatant, erythrocytes were depleted 99.9%, monocytes and granulocytes were depleted 99.9%, B cells were depleted 16.8%, NK cells were depleted 29%, and T cells were depleted 91.5%. In addition, platelets, present in the supernatant at 226×$10^6$/mL before separation, were depleted to 0.3×$10^6$/mL for 99.9% depletion.

TABLE 10

|  | Before separation | After separation |
|---|---|---|
| Erythrocytes per mL | $4.41 \times 10^9$ | $0.005 \times 10^9$ |
| Leukocytes per mL | $5.9 \times 10^6$ | $1.26 \times 10^6$ |
| Lymphocytes (%) | 28.7 | 99.8 |
| Monocytes (%) | 8.69 | 0.06 |
| Granulocytes (%) | 62.5 | 0.09 |
| T Cells (CD3+) | 19.7 | 6.78 |
| B Cells (CD19+) | 4.46 | 69.5 |
| NK Cells (CD16+) | 3.15 | 20.7 |

Example 7

Erythrocyte, CD15+ Cell, CD9+ Cell, and CD72+ Cell Agglutination

The reagent described in Table 11 was used to separate cells according to the method described in Example 1.

TABLE 11

| | |
|---|---|
| Dextran (average molecular weight 413,000) | 20 g/L |
| Dulbecco's phosphate buffered saline (10X) | 100 mL/L |
| Sodium Heparin (10,000 units/mL) | 1 mL/L |
| Hank's balanced salt solution (pH 7.2–7.4) | 50 mL/L |
| Anti-human glycophorin A (murine IgM monoclonal antibody, clone E4) | 1 mg/L |
| Anti-CD15 (murine IgM monoclonal antibody, clone MEM-158) | 1 mg/L |
| Anti-CD9 (murine IgG monoclonal antibody, clone MEM-61) | 1 mg/L |
| Anti-human CD72 paramagnetic agglutination particles (avidin-coated 4.3 micron diameter paramagnetic polystyrene particles labeled with saturating doses of biotin-labeled mouse anti-human CD72, clone BU40) | $2.63 \times 10^9$ particles/L |

Results of a separation are shown in Table 12. In the supernatant, erythrocytes were depleted 99.9%, monocytes were depleted beyond detection, granulocytes were depleted 99.97%, B cells were depleted 97.2%, NK cells were depleted 54.9%. In addition, platelets, present in the supernatant at $226 \times 10^6$/mL before separation, were depleted to $0.1 \times 10^6$/mL for 99.96% depletion.

TABLE 12

|  | Before separation | After separation |
|---|---|---|
| Erythrocytes per mL | $4.41 \times 10^9$ | $0.006 \times 10^9$ |
| Leukocytes per mL | $5.9 \times 10^6$ | $2.3 \times 10^6$ |
| Lymphocytes (%) | 28.7 | 99.9 |
| Monocytes (%) | 8.69 | 0 |
| Granulocytes (%) | 62.5 | 0.1 |
| T Cells (CD3+) | 19.7 | 92.4 |
| B Cells (CD19+) | 4.46 | 0.59 |
| NK Cells (CD16+) | 3.15 | 7.02 |

Example 8

Erythrocyte, CD15+ Cell, CD9+ Cell, CD19+ Cell, and CD16+ Cell Agglutination

The reagent described in Table 13 was used to separate cells according to the method described in Example 1. T cells and CD3+ cells were recovered from the supernatant. B cells and granulocytes are recovered from the agglutinate.

TABLE 13

| | |
|---|---|
| Dextran (average molecular weight 413,000) | 20 g/L |
| Dulbecco's phosphate buffered saline (10X) | 100 mL/L |
| Hank's balanced salt solution (pH 7.2–7.4) | 50 mL/L |
| Sodium Heparin (10,000 units/ml) | 1 mL/L |
| Anti-human glycophorin A (murine IgM monoclonal antibody, clone E4) | 0.1–15 mg/L (preferably about 1.0 mg/L) |
| Anti-human CD15 (murine IgM monoclonal antibody, clone MEM-158) | 0.1–15 mg/L (preferably about 1.0 mg/L) |
| Anti-human CD9 (murine IgM monoclonal antibody, clone MEM-61) | 0.1–15 mg/L (preferably about 1.0 mg/L) |
| Anti-CD19 paramagnetic agglutination particles (avidin-coated 4.3 micron diameter paramagnetic polystyrene particles labeled with saturating doses of biotin-labeled mouse anti-human CD19, clone HIB19) | $0.1$–$30.0 \times 10^9$ particles/L (preferably about $19.8 \times 10^9$ particles/l) |
| Anti-CD16 paramagnetic agglutination particles (avidin-coated 4.3 micron diameter paramagnetic polystyrene particles labeled with saturating doses of biotin-labeled mouse anti-human CD16, clone 3G8) | $5.5 \times 10^{11}$ particles/L |

Example 9

Erythrocyte, CD15+ Cell, CD9+ Cell, CD19+ Cell, CD16+ Cell, and CD4+ Cell Agglutination The reagent described in Table 14 was used to separate cells according to the method described in Example 1. CD8+ cells were recovered from the supernatant.

TABLE 14

| | |
|---|---|
| Dextran (average molecular weight 413,000) | 20 g/L |
| Dulbecco's phosphate buffered saline (10X) | 100 mL/L |
| Sodium Heparin (10,000 units/mL) | 1 mL/L |
| Hank's balanced salt solution (pH 7.2–7.4) | 50 mL/L |
| Anti-human glycophorin A (murine IgM monoclonal antibody, clone E4) | 0.1–15 mg/L (preferably about 1.0 mg/L) |
| Anti-human CD15 (murine IgM monoclonal antibody, clone | 0.1–15 mg/L (preferably |

TABLE 14-continued

| | |
|---|---|
| MEM-158) | about 1.0 mg/L) |
| Anti-human CD9 (murine IgM monoclonal antibody, clone MEM-61) | 0.1–15 mg/L (preferably about 1.0 mg/L) |
| Anti-CD19 paramagnetic agglutination particles (avidin-coated 4.3 micron diameter paramagnetic polystyrene particles labeled with saturating doses of biotin-labeled mouse anti-human CD19, clone HIB19) | $0.1–30.0 \times 10^9$ particles/L (preferably about $19.8 \times 10^9$ particles/L) |
| Anti-CD16 paramagnetic agglutination particles (avidin-coated 4.3 micron diameter paramagnetic polystyrene particles labeled with saturating doses of biotin-labeled mouse anti-human CD16, clone 3G8) | $5.5 \times 10^{11}$ particles/L |
| Anti-CD4 paramagnetic agglutination particles (avidin-coated 4.3 micron diameter paramagnetic polystyrene particles labeled with saturating doses of biotin-labeled mouse anti-human CD4, clone RFT4-γ or clone QS4120) | $1.2 \times 10^{10}$ particles/L |

Example 10

Erythrocyte, CD15+ Cell, CD9+ Cell, CD19+ Cell, CD16+ Cell, and CD8+ Cell Agglutination The reagent described in Table 15 is used to separate cells according to the method described in Example 1. CD4+ cells are recovered from the supernatant.

TABLE 15

| | |
|---|---|
| Dextran (Average molecular weight 413,000) | 20 g/L |
| Dulbecco's phosphate buffered saline (10X) | 100 mL/L |
| Sodium Heparin (10,000 units/mL) | 1 mL/L |
| Hank's balanced salt solution (pH 7.2–7.4) | 50 mL/L |
| Anti-human glycophorin A (murine IgM monoclonal Antibody) clone E4 | 0.1–15 mg/L (preferably about 1.0 mg/L) |
| Anti-human CD15 (murine IgM monoclonal Antibody) (clone MEM-158) | 0.1–15 mg/L (preferably about 1.0 mg/L) |
| Anti-human CD9 (murine IgM monoclonal antibody) (clone MEM-61) | 0.1–15 mg/L (preferably about 1.0 mg/L) |
| Anti-CD19 agglutination particles (avidin-coated 4.3 micron diameter paramagnetic polystyrene particles labeled with saturating doses of biotin-labeled mouse anti-human CD19 (clone HIB19) | $0.1–30.0 \times 10^9$ particles/L (preferably about $19.8 \times 10^9$ particles/L) |
| Anti-CD16 agglutination particle (avidin-coated 4.3 micron diameter paramagnetic polystyrene particles labeled with saturating doses of biotin-labeled mouse anti-human CD16 (clone 3G8) | $5.5 \times 10^{11}$ particles/L |
| Anti-CD8 agglutination particle (avidin-coated 4.3 micron diameter paramagnetic polystyrene particles labeled with saturating doses of biotin-labeled mouse anti-human CD8 (clone HIT8a) | $7.92 \times 10^9$ particles/L |

Example 11

Erythrocyte, CD15+ Cell, CD9+ Cell, CD19+ Cell, and CD2+ Cell Agglutination

The reagent described in Table 16 was used to separate cells according to the method described in Example 1. CD34+ cells were recovered from the supernatant at >50% purity and >80% yield.

TABLE 16

| | |
|---|---|
| Dextran (average molecular weight 413,000) | 20 g/L |
| Dulbecco's phosphate buffered saline (10X) | 100 mL/L |
| Sodium Heparin (10,000 units/mL) | 1 mL/L |
| Hank's balanced salt solution (pH 7.2–7.4) | 50 mL/L |
| Anti-human glycophorin A (murine IgM monoclonal antibody, clone E4) | 0.1–15 mg/L (preferably about 1.0 mg/L) |
| Anti-human CD15 (murine IgM monoclonal antibody, clone MEM-158) | 0.1–15 mg/L (preferably about 1.0 mg/L) |
| Anti-human CD9 (murine IgM monoclonal antibody, clone MEM-61) | 0.1–15 mg/L (preferably about 1.0 mg/L) |
| Anti-CD19 agglutination particles (avidin-coated 4.3 micron diameter paramagnetic polystyrene particles labeled with saturating doses of biotin-labeled mouse anti-human CD19, clone HIB19) | $0.1–30.0 \times 10^9$ particles/L (preferably about $19.8 \times 10^9$ particles/L) |
| Anti-CD2 agglutination particles (avidin-coated 4.3 micron diameter paramagnetic polystyrene particles labeled with saturating doses of biotin-labeled mouse anti-human CD2, clone d118.10.1) | $0.1–30.0 \times 10^9$ particles/L (preferably about $3.0 \times 10^{10}$ particles/L) |

Example 12

Erythrocyte, CD15+ Cell, CD9+ Cell, CD2+ Cell, and CD16+ Cell Agglutination

The reagent described in Table 17 was used to separate cells according to the method described in Example 1. B cells were recovered from the supernatant.

TABLE 17

| | |
|---|---|
| Dextran (average molecular weight 413,000) | 20 g/L |
| Dulbecco's phosphate buffered saline (10X) | 100 mL/L |
| Sodium Heparin (10,000 units/mL) | 1 mL/L |
| Hank's balanced salt solution (pH 7.2–7.4) | 50 mL/L |
| Anti-human glycophorin A (murine IgM monoclonal antibody, clone E4) | 0.1–15 mg/L (preferably about 1.0 mg/L) |
| Anti-human CD15 (murine IgM monoclonal antibody, clone MEM-158) | 0.1–15 mg/L (preferably about 1.0 mg/L) |
| Anti-human CD9 (murine IgM monoclonal antibody, clone MEM-61) | 0.1–15 mg/L (preferably about 1.0 mg/L) |
| Anti-CD2 agglutination particles (avidin-coated 4.3 micron diameter paramagnetic polystyrene particles labeled with saturating doses of biotin-labeled mouse anti-human CD2, clone d118.10.1) | $0.1$–$30.0 \times 10^9$ particles/L (preferably about $3.0 \times 10^{10}$ particles/L) |
| Anti-CD16 agglutination particles (avidin-coated 4.3 micron diameter paramagnetic polystyrene particles labeled with saturating doses of biotin-labeled mouse anti-human CD16, clone 3G8) | $5.5 \times 10^{11}$ particles/L |

Example 13

Erythrocyte, Mature Myeloid Cells, NK Cells, and B Cell Agglutination

Figure 1:
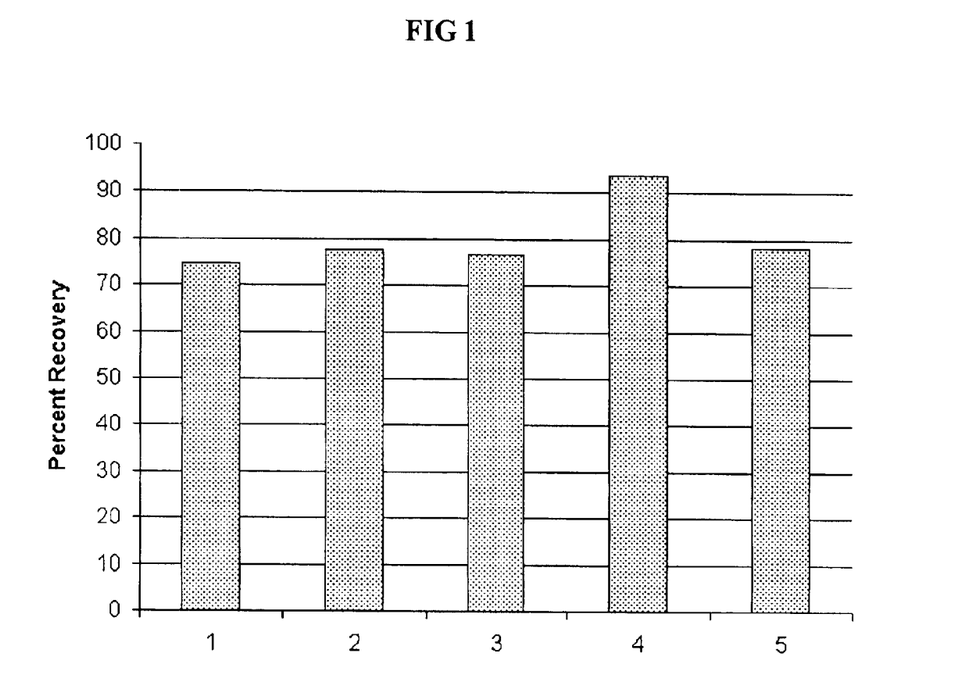
FIG. 1 is a graph of the percent recovery of CD4 T cells from blood samples.
Figure 2:
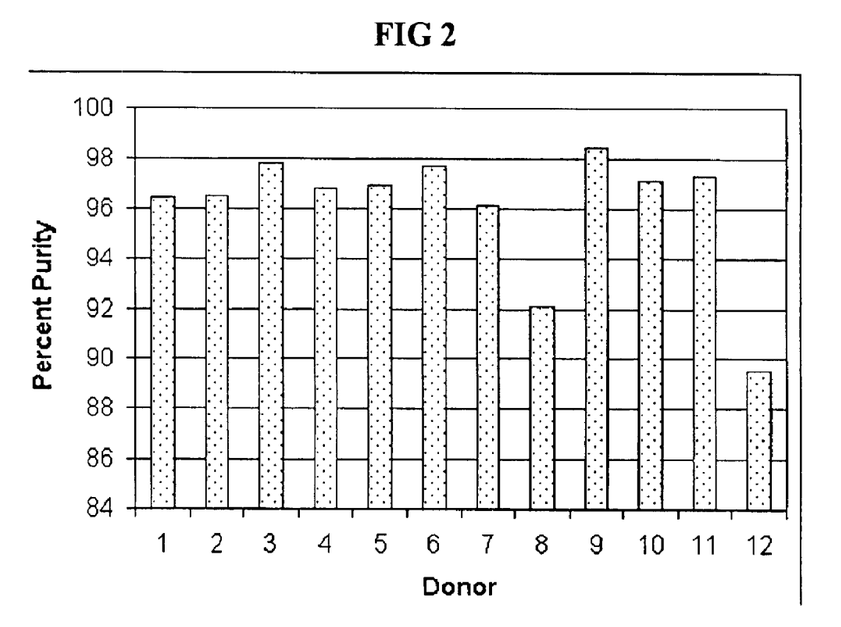
FIG. 2 is a graph of the percent purity of CD4 T cells recovered from blood samples.

The reagent described in Table 18 was used to separate cells according to the method described in Example 1. Hydrochloric acid (4N) or sodium hydroxide (4N) was used to adjust the pH to between 7.2 and 7.4. The anti-CD8, CD16, CD19, CD94, and CD161 antibodies were biotinylated. A cell suspension enriched for CD4 T cells was obtained from the supernatant. Approximately 75 to 94% of the CD4 cells were recovered from each whole blood sample (FIG. 1 provides representative data for five donors). In comparison, cell recovery was 50% or less in other commercially available products that used density-gradient separation. On average, purity of CD4 cells was 96.1% (see FIG. 2, representative data for 12 donors), whereas average purity was 86.7% for CD4 cells purified using other commercially available products that used density-gradient separation.

TABLE 18

| | |
|---|---|
| Dextran (average molecular weight 413,000 | 2% |
| Sodium Heparin (10,000 units/mL) | 1 U/L |
| Hank's balanced salt solution (pH 7.2–7.4) | To final volume |
| Anti-human glycophorin A (murine IgM monoclonal antibody, clone E4) | 1:40 dilution |
| Anti-human CD15 (murine IgM monoclonal antibody, clone MEM-158) | 1 mg/L |
| Anti-human CD9 (murine IgM monoclonal antibody, clone MEM-61) | 1 mg/L |
| Anti-human CD8 (clone HIT8a) | 1 mg/L |
| Anti-human CD16 (clone 3G8) | 1 mg/L |
| Anti-human CD19 (clone HIB19) | 1 mg/L |
| Anti-human CD94 (clone HP-3D9) | 0.125 mg/mL |
| Anti-human CD161 (clone B199.2) | 0.25 mg/mL |

Example 14

Erythrocyte, Mature Myeloid Cells, NK Cells, and B Cell Agglutination

Figure 3:
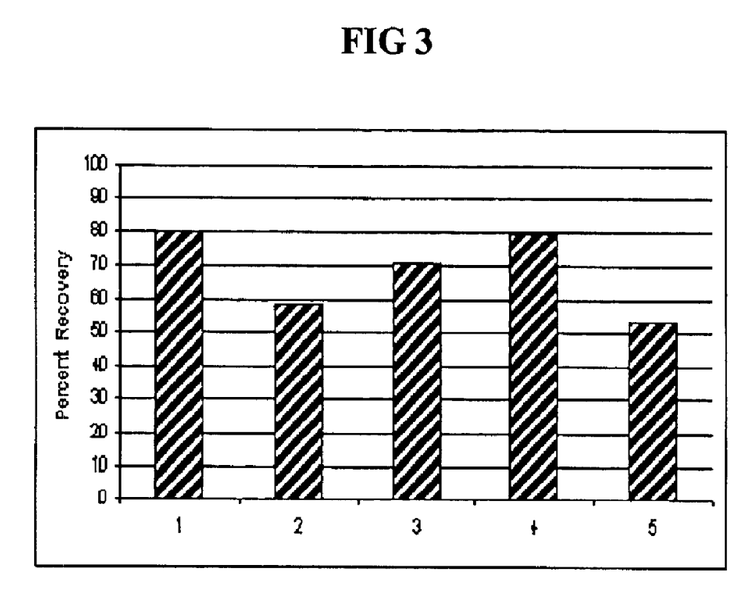
FIG. 3 is a graph of the percent recovery of CD8 T cells from blood samples.
Figure 4:
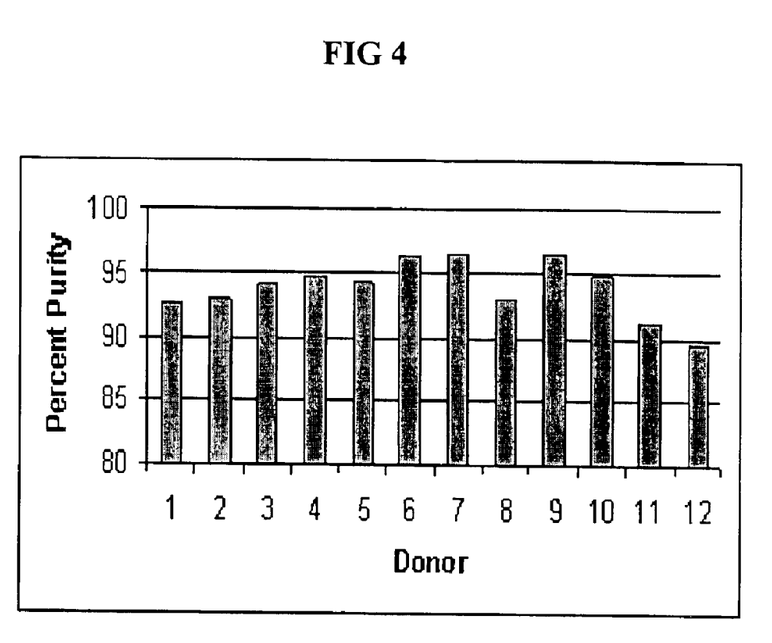
FIG. 4 is a graph of the percent purity of CD8 T cells recovered from blood samples.

The reagent described in Table 19 was used to separate cells according to the method described in Example 1. Hydrochloric acid (4N) or sodium hydroxide (4N) was used to adjust the pH to between 7.2 and 7.4. The anti-CD4, CD16, CD19, CD94, and CD161 antibodies were biotinylated. A cell suspension enriched for CD8 T cells was obtained from the supernatant. Approximately 53 to 81% of the CD8 cells were recovered from each whole blood sample (FIG. 3 provides representative data for five donors). In comparison, cell recovery was less than 52% using other commercially available products that required density-gradient separation, and more typically, cell recovery was less than 35%. On average, purity of CD8 cells was 93.9% (see FIG. 4, representative data for 12 donors), whereas average purity was 84.2% for CD8 cells purified by other commercially available products.

TABLE 19

| | |
|---|---|
| Dextran (average molecular weight 413,000 | 2% |
| Sodium Heparin (10,000 units/mL) | 1 U/L |
| Hank's balanced salt solution (pH 7.2–7.4) | To final volume |
| Anti-human glycophorin A (murine IgM monoclonal antibody, clone E4) | 1:40 dilution |
| Anti-human CD15 (murine IgM monoclonal antibody, clone MEM-158) | 1 mg/L |
| Anti-human CD9 (murine IgM monoclonal antibody, clone MEM-61) | 1 mg/L |
| Anti-human CD4 (clone QS4120) | 1 mg/L |
| Anti-human CD16 (clone 3G8) | 1 mg/L |
| Anti-human CD19 (clone HIB19) | 1 mg/L |
| Anti-human CD94 (clone HP-3D9) | 0.25 mg/mL |
| Anti-human CD161 (clone B199.2) | 1 mg/mL |

Other Embodiments

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A composition comprising:
   a) dextran;
   b) anti-glycophorin A antibody;
   c) anti-CD15 antibody;
   d) anti-CD9 antibody;
   e) anti-CD94 antibody; and
   f) anti-CD161 antibody.

2. The composition of claim 1, said composition further comprising anti-CD72 antibody.

3. The composition of claim 1, said composition further comprising anti-CD4 antibody, anti-CD16 antibody, and anti-CD19 antibody.

4. The composition of claim 1, said composition further comprising anti-CD8 antibody, anti-CD16 antibody, and anti-CD19 antibody.

5. The composition of claim 1, said composition further comprising anti-CD2 antibody.

6. The composition of claim 1, further comprising heparin.

7. The composition of claim 1, further comprising divalent cations.

8. The composition of claim 7, wherein said divalent cations are $Ca^{+2}$.

9. The composition of claim 7, wherein said divalent cations are $Mg^{+2}$.

10. The composition of claim 1, further comprising phosphate buffered saline.

11. The composition of claim 1, wherein the pH of said composition is between 6.8 to 7.8.

12. The composition of claim 1, wherein the pH of said composition is between 7.2 to 7.4.

13. The composition of claim 1, wherein said anti-glycophorin A antibody is monoclonal.

14. The composition of claim 1, wherein said anti-glycophorin A antibody is an IgM antibody, or an IgG antibody.

15. The composition of claim 1, wherein said anti-glycophorin A antibody is an anti-human glycophorin A antibody.

16. The composition of claim 1, wherein the concentration of said anti-glycophorin A antibody is about 0.1 mg/L to about 15 mg/L.

17. The composition of claim 1, wherein said anti-CD15 antibody is a monoclonal antibody.

18. The composition of claim 1, wherein said anti-CD15 antibody is an IgM antibody or an IgG antibody.

19. The composition of claim 1, wherein said anti-CD15 antibody is an anti-human CD15 antibody.

20. The composition of claim 1, wherein the concentration of said anti-CD15 antibody is about 0.1 mg/L to about 15 mg/L.

21. The composition of claim 1, wherein said anti-CD9 antibody is a monoclonal antibody.

22. The composition of claim 1, wherein said anti-CD9 antibody is an IgM antibody, or an IgG antibody.

23. The composition of claim 1, wherein said anti-CD9 antibody is an anti-human CD9 antibody.

24. The composition of claim 1, wherein the concentration of said anti-CD9 antibody is at about 0.1 mg/L to about 15 mg/L.

25. The composition of claim 1, wherein the concentration of said anti-CD94 antibody is 0.01 mg/L to 10 mg/L.

26. The composition of claim 1, wherein the concentration of said anti-CD161 antibody is 0.01 mg/L to 10 mg/L.

27. The composition of claim 1, wherein said anti-CD94 antibody is an IgM or IgG antibody.

28. The composition of claim 1, wherein said anti-CD161 antibody is an IgM or IgG antibody.

29. The composition of claim 1, wherein said anti-CD94 antibody is an anti-human CD94 antibody.

30. The composition of claim 1, wherein said anti-CD161 antibody is an anti-human CD161 antibody.

31. A composition comprising:
a) dextran;
b) anti-glycophorin A antibody;
c) anti-CD15 antibody;
d) anti-CD9 antibody;
e) anti-CD4 antibody or anti-CD8 antibody;
f) anti-CD16 antibody;
g) anti-CD19 antibody;
h) anti-CD94 antibody;
i) anti-CD161 antibody;
j) heparin; and
k) divalent cations.

32. The composition of claim 31, wherein said composition contains anti-CD4 antibody.

33. The composition of claim 31, wherein said composition contains anti-CD8 antibody.

34. The composition of claim 31, wherein at least one of said antibodies is biotinylated.

35. The composition of claim 34, wherein said anti-CD16 antibody, said anti-CD19 antibody, said anti-CD94 antibody, and said anti-CD161 antibody are biotinylated.

36. A kit comprising a blood collection vessel and the cell separation composition of claim 31.

37. The kit of claim 36, wherein said blood collection vessel is a blood bag.

38. The kit of claim 36, wherein said blood collection vessel is a vacuum tube.

39. A method for separating cells, said method comprising:
a) contacting a blood cell-containing sample with a composition, said composition comprising:
i) dextran;
ii) anti-glycophorin A antibody;
iii) anti-CD15 antibody;
iv) anti-CD9 antibody;
v) anti-CD94 antibody; and
vi) anti-CD161 antibody.
b) allowing said sample to partition into an agglutinate and a supernatant phase; and
c) recovering cells from either or both the agglutinate or supernatant phase.

40. The method of claim 39, wherein said composition further comprises anti-CD4 antibody, anti-CD16 antibody, and anti-CD19 antibody.

41. The method of claim 39, wherein said composition further comprises anti-CD8 antibody, anti-CD16 antibody, and anti-CD19 antibody.

42. The method of claim 39, wherein said sample is derived from a human.

43. The method of claim 42, wherein said sample is a peripheral blood sample.

44. The method of claim 42, wherein said sample is an umbilical cord sample.

45. The method of claim 42, wherein said sample is a bone marrow sample.

46. The method of claim 42, wherein said cells are metastatic tumor cells.

47. The method of claim 42, wherein said cells are recovered from said supernatant phase.

48. The method of claim 47, wherein said cells are stem cells.

49. The method of claim 39, wherein said anti-CD94 antibody and said anti-CD161 antibody are biotinylated.

50. The method of claim 49, wherein recovery of said cells comprises contacting said supernatant phase with a composition comprising avidin-coated particles, separating said supernatant phase and said composition comprising avidin-coated particles, and recovering cells from said supernatant phase.

* * * * *

UNITED STATES PATENT AND TRADEMARK OFFICE
CERTIFICATE OF CORRECTION

PATENT NO. : 6,933,148 B2
DATED : August 23, 2005
INVENTOR(S) : Daniel P. Collins, Joel H. Hapke and Carol A. Buchert

It is certified that error appears in the above-identified patent and that said Letters Patent is hereby corrected as shown below:

Title page,
Item [56], References Cited, OTHER PUBLICATIONS, "Rubinstein et al." reference, delete "12" and insert -- 22 --.

Column 20,
Line 28, delete "." and insert -- ; --.

Signed and Sealed this

Fourteenth Day of March, 2006

JON W. DUDAS
*Director of the United States Patent and Trademark Office*